United States Patent [19]

Juguin et al.

[11] Patent Number: 5,177,280
[45] Date of Patent: Jan. 5, 1993

[54] PROCESS FOR PRODUCING ALKYLBENZENES USING A CATALYST BASED ON A DEALUMINIZED Y ZEOLITE AND A CATALYST BASED ON A DEALUMINIZED MORDENITE

[75] Inventors: Bernard Juguin; Pierre Dufresne, both of Rueil-Malmaison; Francis Raatz, Acheres; Germain Martino, Poissy, all of France

[73] Assignee: Institut Francais du Petrole, Rueil-Malmaison, France

[21] Appl. No.: 534,229

[22] Filed: Jun. 7, 1990

[30] Foreign Application Priority Data

Jun. 7, 1989 [FR] France ................................ 89 07633

[51] Int. Cl.⁵ ........................... C07C 2/64; C07C 5/52
[52] U.S. Cl. .................................. 585/323; 585/467; 585/475
[58] Field of Search ....................... 585/323, 475, 467

[56] References Cited

U.S. PATENT DOCUMENTS

| | | | |
|---|---|---|---|
| 4,083,886 | 4/1978 | Michalco | 585/475 |
| 4,169,111 | 9/1979 | Wight | 585/323 |
| 4,459,426 | 7/1984 | Inwood et al. | 585/323 |
| 4,870,222 | 9/1989 | Bakas et al. | 585/323 |

OTHER PUBLICATIONS

Gnep et al., "Creation de mesopores dans des zeolithes monodimensionnelles. Une methode pour ameliorer leur stabilite catalytique," C. R. Acad. Sci. Paris, vol. 309, Series 11, pp. 1743–1747, 1989.

*Primary Examiner*—Asok Pal
*Assistant Examiner*—P. Achutamurthy
*Attorney, Agent, or Firm*—Millen, White, Zelano and Branigan

[57] ABSTRACT

The invention relates to a process for producing an alkylbenzene from benzene and an aliphatic mono-olefin in the presence of a catalyst based on a dealuminized Y zeolite with a molar ratio $SiO_2/Al_2O_3$ ranging from 8 to 70, the product of this reaction being afterwards fractionated into a first fraction containing non converted benzene and a mono-alkylbenzene and a second fraction containing a poly-alkylbenzene, said second fraction reacting then with benzene in the presence of a catalyst based on a dealuminized mordenite with a total atomic ratio Si/Al ranging from 30 to 80. The invention especially applies to the production of ethylbenzene and cumene respectively from ethylene and propene.

18 Claims, No Drawings

5,177,280

PROCESS FOR PRODUCING ALKYLBENZENES USING A CATALYST BASED ON A DEALUMINIZED Y ZEOLITE AND A CATALYST BASED ON A DEALUMINIZED MORDENITE

BACKGROUND OF THE INVENTION

The present invention relates to a process for producing at least one alkylbenzene by alkylation of the benzene by means of mono-olefin(s). The original monoolefin or mixture of mono-olefins may stem from any well-known source, for example from catalytic cracking or steam-cracking units.

The use of zeolites in the H form, particularly the ZSM5, has already been suggested for carrying out this reaction (European Pat. No. 104,729).

More recently, other zeolites have been put forward, particularly certain mordenites, alone or mixed with faujasite (U.S. Pat. No. 3,436,432), possibly with a metal from group VIII deposited on it (U.S. Pat. No. 3,851,004). Japanese Patents No. 58,216,128 and 58,159,427 recommend mordenites alone, with a low Si/Al ratio (4.5 to 5), containing metallic ions such as Mg, K, Ca, or in the H$^-$ form (Japanese Pat. No. 041,670).

Still more recently, a French patent application (national registration number 88/14,099) reports satisfactory results obtained in the presence of dealuminized mordenites with a total atomic ratio Si/Al ranging from 30 to 80.

SUMMARY OF THE INVENTION

The object of the invention is notably to improve the alkylation yield in mono-alkylbenzenes, by reducing the proportion of formed poly-alkylbenzenes.

DETAILED DESCRIPTION OF THE INVENTION

According to the process of the invention, the benzene is first reacted (first stage or alkylation stage) with a charge comprising at least one aliphatic mono-olefin in contact with at least one catalyst based on a dealuminized Y zeolite with a molar ratio $SiO_2/Al_2O_3$ ranging from 8 to 70, the product is fractionated in order to separately recover a first fraction containing non converted benzene and at least one mono-alkylbenzene and a second polyalkylbenzene fraction (i.e. a fraction comprising at least one poly-alkylbenzene).

In a second stage (transalkylation stage), at least part of said poly-alkylbenzene fraction is reacted with benzene, for example with a benzene at least part of which consists of benzene which has not been converted in the first stage (i.e. non converted benzene stemming from said first fraction in the first stage) or for example with benzene at least part of which does not consist of benzene not converted in the first stage, in contact with at least one catalyst based on a dealuminized mordenite with a total atomic ratio Si/Al ranging from 30 to 80, and at least one mono-alkylbenzene is recovered.

The excess benzene of the first stage which has not been sent to the second stage is advantageously recycled in the first stage, whereas, after the second stage, the non converted poly-alkylbenzenes can be recycled in the same second stage.

Thus, the mono-alkylbenzenes obtained through the process in two stages according to the invention stem, on one hand, from the first fraction obtained in the first stage (this fraction itself can be fractionated into non converted benzene and in at least one mono-alkylbenzene), and, on the other hand, from the reaction (second stage) of the second fraction obtained in the first stage with benzene.

The dealuminized Y zeolite and the dealuminized mordenite are each used alone or mixed with a binder or a matrix generally selected from the group consisting of the clays, the aluminas, silica, magnesia, zircon, titanium oxide, boron oxide and any combination of at least two of the compounds cited above, such as silica-alumina, silica-magnesia, etc. Any well-known agglomeration or shaping method can be applied, such as, for example, extrusion, pelletizing, oil drop, etc.

Thus, the process according to the invention utilizes at least one catalyst based on dealuminized Y zeolite with a molar ratio $SiO_2/Al_2O_3$ ranging form 8 to 70, generally containing 1 to 100%, preferably 20 to 98% and for example 40 to 98% by weight of said dealuminized Y zeolite and 0 to 99%, preferably 2 to 80% and for example 2 to 60% by weight of a matrix, and at least one catalyst based on dealuminized mordenite with a total atomic ratio Si/Al ranging from 30 to 80, generally containing 1 to 100%, preferably 20 to 98% and for example 40 to 98% by weight of said dealuminized mordenite and 0 to 99%, preferably 2 to 80% and for example 2 to 60% by weight of a matrix.

Dealuminized Y zeolites and their preparation are well-known. It can for example be referred to U.S. Pat. No. 4,738,940.

The Y zeolite which is used in the present invention is a HY acid zeolite characterized by various specifications the determination methods of which are given further on: a molar ratio $SiO_2/Al_2O_3$ ranging from 8 to 70 and, more preferably, from about 12 to 40; a sodium content lower than 0.25% by weight determined on the zeolite calcined at 1100° C.; a crystalline parameter a of the unit cell ranging from $24.55 \times 10^{-10}$ to $24.24 \times 10^{-10}$ m and preferably from $24.39 \times 10^{-10}$ to $24.26 \times 10^{-10}$ m; a sodium ion recovery capacity $C_{Na}$, expressed in gram of Na per 100 grams of modified, neutralized, then calcined zeolite, higher than about 0.85 (the capacity $C_{Na}$ for recovering sodium ions will be defined more precisely in the following paragraph); a specific surface, determined with the B.E.T. method, higher than about 400 $m^2/g$ and preferably higher than 550 $m^2/g$; a capacity for adsorbing steam at 25° C., for a partial pressure of 2.6 torrs, higher than about 6%; a pore-size distribution such that between 1 and 20%, and preferably between 3 and 15% of the pore volume contained in pores having a diameter ranging from $20 \times 10^{-10}$ to $80 \times 10^{-10}$ m, the remainder of the pore volume being pores having a diameter smaller than $20 \times 10^{-10}$ m.

The various features cited above can be measured by the following methods:

the molar ratio $SiO_2/Al_2O_3$ can be measured through a chemical analysis. When the amounts of aluminum become low, for example less than 2%, in view of a greater precision, it is advisable to use a calibration method by atomic adsorption spectrometry;

the unit cell parameter can be calculated form the X ray diffraction diagram, according to the method described in the ASTM D 3.942-80 sheet. It is obvious that, in order to carry out this calculation correctly, the crystallinity of the product must be sufficient;

the specific surface is for example determined by measuring the nitrogen adsorption isotherm at the liquid nitrogen temperature and calculated according to the conventional B.E.T. method. The samples are pretreated before measuring at 500° C. under dry nitrogen scavenging;

the pore-size distribution can be determined by the B.J.H. method described by BARRET, JOYNER and HALENDA in Journal of American Chemical Society, Vol. 73, p.373, 1951. This method is based on the numerical exploitation of the nitrogen desorption isotherm The measuring is carried out with a CARLO ERBA device of the SORPTOMATIC 1800 type. The results are expressed by the values of the pore volume V according to the diameter D of the pores; the derived curve is also given: dV/dD according to D. The total pore volume is defined here as the volume of nitrogen adsorbed at saturation point, more exactly at a partial pressure corresponding to a ratio between the partial pressure and the saturated vapor-pressure P/Po equal to 0.99;

the water recovery percentages (or steam adsorption capacity) are for example determined with a conventional gravimetry equipment. The sample is pretreated at 400° C. under rough vacuum, then brought up to a stable temperature of 25° C. A water pressure of 2.6 torrs is then admitted, which corresponds to a P/Po ratio of about 0.10 (ratio between the partial pressure of water admitted in the device and the saturated vapor-pressure of the water at the temperature of 25° C.);

the sodium ion exchange capacity $C_{Na}$ (or sodium ions recovery capacity) can be determined as follows: one gram of zeolite is subjected to three successive exchanges in 100 cm$^3$ of a 0.2M solution of NaCl, for one hour at 20° C. under proper stirring. The natural pH value of the solutions is maintained during the exchange. As a matter of fact, if the pH value were readjusted to values close to 7, by adding small amounts of soda, the exchanged sodium rates would be higher. It is expressed in gram of sodium per 100 grams of modified zeolite.

It has been discovered in the present invention that the stabilized Y zeolites answering the specifications cited above show remarkable properties for the production of mono-alkylbenzenes by alkylation of the benzene by means of mono-olefin(s).

These zeolites are for example manufactured, generally from a Y-Na zeolite, by an appropriate combination of two basic treatments (a) a hydrothermal treatment which associates temperature and steam partial pressure, and (b) an acid treatment by a preferably strong and concentrated mineral acid.

Generally, the Y-Na zeolite from which the Y zeolite used in the invention is prepared has a molar ratio $SiO_2$/$Al_2O_3$ ranging from about 4 to 6; it is previously advisable to decrease its content by weight of sodium to less than 3% and preferably to less than 2.5%; the Y-Na zeolite also generally shows a specific surface ranging from about 750 to 950 m$^2$/g.

The dealuminized mordenites and their preparation are also well-known. It can for example be referred to European Patents No. 084,748, 097,552 and 196,965 and to the French patent application of national registration number 87/12,932. The dealuminizing method of the patents or of the application cited above consists in subjecting the H form of the mordenite or a precursor of the H form (for example the NH$_4$ form) to a series of treatment in a steam atmosphere and of acid treatments. Nonetheless, unlike the treatments of said documents cited above, the dealuminizing rate will be here limited to a total atomic ratio Si/Al ranging from 30 to 80. In fact, European Pat. No. 084,748, p.4, describes preparations resulting in total atomic ratios Si/Al of 46 and 82 for example. It is preferably operated as follows:

in a first stage, the non decomposable cations, generally Na$^-$, which are present in the original mordenite are removed. To do so, one or several exchanges can be carried out in diluted solutions of acids such as HCl or in NH$_{4+}$ solutions, optionally followed by one or several washings (for example with water). The important point is that, at the end of this first stage which may be called decationizing, the near total of the alkaline cations is removed (Na content for example ranging from 150 to 2,000 ppm by weight and preferably from 300 to 1,200 ppm by weight) and that the obtained solid is an H form or a precursor with an H form (for example NH$_{4+}$) substantially not dealuminized (dealumination rate generally lower than 10% and preferably than 5%). More preferably, the NH$_{4+}$ form will be chosen as an H form precursor;

in a second stage, the H form or the H form precursor is subjected to a steam treatment at a temperature over 450° C., ranging for example from 450° to 650° C. and preferably from 550° to 600° C. The water content (by volume) of the calcination atmosphere will be advantageously higher than 20% and preferably than 40%;

acid attack is the third stage of the catalyst preparation. For structure atomic ratios Si/Al (of the solid after calcining) up to about 50, acid solution concentrations (HCl, H$_2$SO$_4$, HNO$_3$, etc.) ranging from 0.5 to 5N and preferably from 1 to 4N will be preferably used. For higher structure atomic ratios Si/Al, acid solution concentrations ranging from 5 to 20N and preferably from 7 to 12N will be utilized (the structure atomic ratios Si/Al can be determined by infrared spectroscopy for ratios ranging from 10 to 50 and by NMR of the $^{29}$Si for higher ratios). Besides, in order to reach high atomic ratios Si/Al, that is to say higher than about 50 and more specifically higher than about 60, several calcination under steam-acid attack cycles can be advantageously performed.

The solids prepared accordingly advantageously show total atomic ratios Si/Al ranging from 30 to 80; their unit cell volume ranges form 2.755 to 2.730 nm$^3$ (1 mn=10$^{-9}$ m) and preferably from 2.745 to 2.735 nm$^3$; their acid strength is preferably sufficient for the structural Al-OH to interact with a weak base such as ethylene (infrared measuring at 77K) or a compound with weak acid features such as H$_2$S (infrared measuring at 25° C.). Besides, these solids must also be preferably free from extra-lattice cationic species which can be detected by a fine signal (width at half height lower than 5 ppm and preferably lower than 2 ppm) located at 0 ppm (reference Al(H$_2$)$_6^{3+}$) on an NMR spectrum of $^{27}$Al, measured with the magic angle rotation technique.

The reaction known as alkylation reaction is usually carried out in the liquid phase, in the supercritical phase or in the gaseous phase, in the presence of at least one catalyst based on the dealuminized Y zeolite defined above, arranged in a fixed bed, at a temperature ranging from about 50° to 450° C. (preferably from about 100° to 350° C.), under a pressure of 1 to 10 MPa (preferably 2 to 7 MPa), with a liquid hydrocarbon flow rate (space velocity) ranging from about 0.5 to 50 volumes per volume of catalyst and per hour, and with a molar ratio benzene/mono-olefins ranging from 1 to 20 (preferably from 3 to 7 for propene and from 7 to 12 for ethylene).

The reaction known as transalkylation of the polyalkylbenzenes formed during the alkylation stage is usually carried out in the presence of at least one catalyst based on the dealuminized mordenite defined above, arranged in a fixed bed, at a temperature ranging from about 200° to 500° C. (preferably from about 280° to 400° C.), under a pressure of 2 to 10 MPa (preferably 2.5 to 7 MPa), with a liquid hydrocarbon flow rate (space velocity) ranging from about 0.5 to 5 volumes per volume of catalyst and per hour, and with a molar ratio benzene/poly-alkylbenzenes ranging from 2 to 50.

Although the invention can be implemented with a mixture of mono-olefins, for example a catalytic cracking effluent, it is preferred, in order to facilitate the fractionating between the mono-alkylbenzenes and the polyalkylbenzenes, to operate with only one mono-olefin, for example ethylene, propylene, a n-butene or isobutene, more generally with an aliphatic mono-olefin with for example 2 to 20 atoms of carbon.

Treating mixtures of mono-olefins with carbon oxide, for example 0.1 to 2.0% by weight, which is often the case with cracking effluents, is particularly interesting. As a matter of fact the presence of carbon oxide has no harmful effect, contrary to what has been observed with the conventional catalysts containing nickel.

In order to simplify the implementing of the invention, it is possible to use only one distillation zone for the effluents from the two stages of the process (alkylation + transalkylation) according to a technique well-known by the man skilled in the art.

The following examples illustrate the present invention without limiting the scope thereof.

EXAMPLE 1

Preparation of a catalyst A

The raw material which is used is a NaY zeolite of formula $NaAlO_2 (SiO_2)_{2.5}$.

This zeolite shows the following features:
molar ratio $SiO_2/Al_2O_3$: 3
crystalline parameter a: $24.69 \times 10^{-10}$ m
steam adsorption capacity at 25° C. (at $P/Po=0.1$): 26%
specific surface: 880 m²/g.

It is subjected to five successive exchanges in ammonium nitrate solutions with a concentration of 2M, at a temperature of 95° C., for 1.5 hour, and with a ratio volume of solution to weight of zeolite equal to 8 cm³/g. The sodium rate of the obtained $NaNH_4Y$ zeolite is 0.95%. This product is then rapidly introduced into a furnace preheated up to 770° C. and let for 4 hours in a static atmosphere (stabilizing treatment). The zeolite is then subjected to two exchanges by ammonium nitrate solutions with a concentration of 2M, so that its sodium content decreases to 0.2% by weight. Its molar ratio $SiO_2/Al_2O_3$ is then 6.3, its crystalline parameter a of the unit cell is $24.38 \times 10^{-10}$ m, its specific surface is 625 m²/g, its water recovery capacity is 11.3% (at $P/Po=0.1$), its sodium ion recovery capacity is 2 and 11% of its pore volume is contained in pores with a diameter ranging from $20 \times 10^{-10}$ to $80 \times 10^{-10}$ m, the rest of its pore volume being pores having a diameter smaller than $20 \times 10^{-10}$ m. The zeolite obtained accordingly is shaped by extrusion with alumina. The obtained extrudates are then dried and calcined at about 500° C. A catalyst A based on said zeolite, containing 80% by weight of said zeolite and 20% by weight of alumina, is then obtained.

EXAMPLE 2

Preparation of a catalyst B

The original NaY zeolite is subjected to the same five exchanges and to the same stabilizing treatment as in example 1. After stabilizing, instead of carrying out exchanges with ammonium ions, an acid treatment is performed in the following conditions: the ratio of the volume of 2N nitric acid solution to the weight of solid is 6 cm³/g, the temperature is 95° C. and the treatment duration is 3 hours. Then, another treatment is carried out in the same conditions, but with a 0.3N nitric acid solution.

The obtained zeolite shows a content per weight of sodium of 0.2%, a molar ratio $SiO_2/Al_2O_3$ of 18, a crystalline parameter a of the unit cell of $24.32 \times 10^{-10}$ m, a specific surface of 805 m²/g, a water recovery capacity of 13.7% (at $P/Po=0.1$), a sodium ions recovery capacity of 2 and 9% of its pore volume is contained in pores with a diameter ranging from $20 \times 10^{-10}$ to $80 \times 10^{-10}$ m, the rest of its pore volume being contained in pores having a diameter smaller than $20 \times 10^{-10}$ m.

The shaping, drying and calcining stages are carried out in the same conditions as those described in example 1, in order to obtain a catalyst B based on said zeolite, containing 80% by weight of said zeolite and 20% by weight of alumina.

EXAMPLE 3

Preparation of a catalyst C

The original catalyst C is subjected to the same five exchanges and to the same stabilizing treatment as in example 1.

After stabilizing, instead of carrying out exchanges with ammonium ions, an acid treatment is performed by means of a 2N nitric acid solution in the following conditions: the ratio of the volume of 2N nitric acid solution to the weight of the solid is 6 cm³/g, the temperature is 95° C. and the treatment duration is 3 hours. Then, another treatment is carried out in the same conditions, but with a 3N nitric acid solution.

The obtained zeolite has a content by weight of sodium of 0.2%, a molar ratio $SiO_2/Al_2O_3$ of 75, a crystalline parameter a of the unit cell of $24.28 \times 10^{-10}$ m, a specific surface of 795 m²/g, a water recovery capacity of 13.5% (at $P/Po=0.1$), a sodium ion recovery capacity of 2 and 10% of its pore volume is contained in pores with a diameter ranging from $20 \times 10^{-10}$ m to $80 \times 10^{-10}$ m, the rest of its pore volume being pores having a diameter smaller than $20 \times 10^{-10}$ m.

The shaping, drying and calcining stages are performed in the same conditions as those described in example 1, in order to obtain a catalyst C based on said zeolite, containing 80% by weight of said zeolite and 20% by weight of alumina.

EXAMPLE 4

Preparation of a catalyst D

The raw material which is used for preparing this catalyst is a small pore-mordenite manufactured by the Société Chimique de la Grande Paroisse, reference Alite 150; its chemical formula in the anhydrous state is $Na_8AlO_2(SiO_2)_{5.5}$ and its content by weight of sodium is 5.3%. 500 grams of this powder are immersed into a 2M ammonium nitrate solution, and the suspension is brought up to 95° C. for 2 hours. The volume of the ammonium nitrate solution which is used is 4 times the weight of the dry mordenite (V/W=4 g/cm³). This cationic exchange operation is performed three times. After the third exchange, the product is washed with water at 20° C. for 20 minutes, with a ratio V/W equal 4 to 4 g/cm³. The sodium content expressed in percentage by weight in relation to the dry mordenite is only 0.1%. The product is then filtered and subjected to a self-steaming calcination at 560° C. for 2 hours. The water content (by volume) of the calcination atmosphere is about 90%. The crystallinity of this solid, after this calcination stage, is higher than or equal to 90%; its structure atomic ratio Si/Al is 49.

This solid is then subjected to an acid attack by means of a 3.5N nitric acid solution. During the acid attack, the solid is subjected to the nitric acid solution for 2 hours, with a ratio W/V equal to 8 g/cm³. The product is then filtered and abundantly washed with distilled water.

The obtained mordenite has a total atomic ratio Si/Al of 49; its unit cell volume is 2.74 nm³.

It is thereafter shaped by malaxing with alumina, then by passing across a die. The obtained extrudates, with a diameter of 1.2 mm, are then dried, and calcined between 150° and 500° C., following stages of about one hour. Catalyst D based on said mordenite is thus obtained, which contains 80% by weight of said mordenite and 20% by weight of alumina.

EXAMPLE 5

Each one of the three catalysts A, B and C prepared in examples 1, 2 and, 3 is tested in the alkylation of benzene by ethylene under the following operating conditions (in a reactor known as "alkylation reactor"):

| temperature | 270° C. |
|---|---|
| pressure | 3 MPa |
| hourly flow by weight of benzene is equal to | 2 x catalyst weight |
| molar ratio benzene/ethylene | 9. |

The composition by weight of the charge is the following:

| ethylene | 3.73% |
|---|---|
| benzene | 96.27%. |

At the reactor outlet, the obtained products have the composition by weight shown in Table I. It can be noticed that it is preferable to operate, during the alkylation stage, with the catalysts recommended by the invention, which means that dealuminized Y zeolites with a molar ratio $SiO_2/Al_2O_3$ ranging from 8 to 70 (case of catalyst B) should be utilized. As a matter of fact, the Y zeolites with a molar ratio $SiO_2/Al_2O_3$ lower than 8 (case of catalyst A) are slightly more active, but noticeably less selective and less stable. On the contrary, the Y zeolites with a molar ratio $SiO_2/Al_2O_3$ higher than 70 (case of catalyst C) are a little more selective, but much less active, which might require for industrial operation, either a markedly higher temperature leading to lower cycle durations, or lower space velocities, which would be a disadvantage for the economy of the process.

TABLE I

| CATALYSTS | CHARGE | A | B | C |
|---|---|---|---|---|
| CONSTITUENTS (% by wt.) | | | | |
| Ethylene | 3.73 | — | 0.01 | 1.42 |
| Benzene | 96.27 | 87.12 | 86.28 | 90.02 |
| Toluene | — | 0.03 | — | — |
| Ethylbenzene | — | 11.05 | 13.10 | 8.25 |
| Methylethylbenzenes | — | 0.04 | — | — |
| Diethylbenzenes | — | 1.17 | 0.55 | 0.29 |
| Methyldiethylbenzenes | — | 0.03 | — | — |
| Triethylbenzenes | — | 0.31 | 0.04 | 0.02 |
| Heavy aromatic HC | — | 0.25 | 0.02 | — |
| | | 100 | 100 | 100 |
| CONVERSION COEFFICIENT PER PASS | | | | |
| Ethylene | | 100% | 99.7% | 61.9% |
| Benzene | | 9.5% | 10.4% | 6.5% |
| SELECTIVITIES | | | | |
| $\frac{Ethylbenzene}{Converted\ ethylene} \cdot 100$ | | 78.3% | 93.0% | 94.3% |
| $\frac{Ethylbenzene}{Converted\ ethylene} \cdot 100$ | | 88.8% | 96.5% | 97.2% |

After the reaction, the product obtained in the presence of catalyst B is fractionated by distillation, and two fractions are recovered:

a 140° C.-initial point fraction containing the non converted benzene and the ethylbenzene, a fraction with a boiling point higher than 140° C. containing the polyethylbenzenes and the heavy aromatic hydrocarbons (HC).

This fraction with a boiling point higher than 140° C. is thereafter subjected to a transalkylation treatment in the presence of catalyst D (prepared in example 4) under the following operating condition (in a reactor known as "transalkylation reactor"):

| temperature | 360° C. |
|---|---|
| pressure | 3 MPa |
| flow rate by weight of charge (polyethylbenzenes + heavy aromatic hydrocarbons + additional benzene stemming from the product of the alkylation reaction) is equal to | 1 x catalyst weight |
| molar ratio benzene/polyethylbenzenes: | 16. |

The results that are obtained (through the transalkylation treatment) are shown in Table II.

The overall results combining the two stages of alkylation on one hand and of transalkylation on the other hand are the following:

| | |
|---|---|
| benzene conversion coefficient | 10.7% |
| ethylene conversion coefficient | 99.7% |
| ethylbenzene selectivity in relation to the converted ethylene | 98.7% |
| ethylbenzene selectivity in relation to the converted benzene | 99.4% |

As for the industrial implementation of this type of process, the diethylbenzenes and the triethylbenzenes which have not been converted after the transalkylation stage are recycled till destruction in the transalkylation reactor; in this case, by using catalysts B (in the alkylation stage) and D (in the transalkylation stage), the ultimate performances are the following:

| | |
|---|---|
| 1) Conversion coefficient: | |
| benzene | 10.7% |
| ethylene | 99.7% |
| 2) Selectivities: | |
| ethylbenzene in relation to the converted benzene | 99.4% |
| ethylbenzene in relation to the converted ethylene | 99.6% |

TABLE II

| CONSTITUENTS | CHARGE | PRODUCT |
|---|---|---|
| Benzene | 5.58 | 5.29 |
| Ethylbenzene | — | 0.79 |
| Diethylbenzenes | 0.55 | 0.07 |
| Triethylbenzenes | 0.04 | 0.01 |
| Heavy aromatic HC | 0.02 | 0.03 |
| | 6.19 | 6.19 |
| CONVERSION COEFFICIENT PER PASS | | |
| Benzene | | 5.2% |
| Diethylbenzenes | | 87.3% |
| Triethylbenzenes | | 75.0% |
| SELECTIVITY | | |
| $\frac{\text{Ethylbenzene}}{\text{Converted (diethylbenzenes + triethylbenzenes)}} \cdot 100$ | | 98.8% |

EXAMPLE 6

This example is operated under the same conditions as in example 5, especially by using catalyst B in the alkylation section and catalyst D in the transalkylation section, while changing the molar ratio benzene/ethylene at the alkylation reactor inlet in order to show the significance of this parameter concerning the activity and especially the selectivity of the catalysts. The overall results combining the two stages of alkylation on one hand and of transalkylation on the other hand are shown in Table III.

TABLE III

| molar $\frac{\text{BENZENE}}{\text{ETHYLENE}}$ | 5.1 | 9.3 | 13.7 |
|---|---|---|---|
| RESULTS CONVERSION COEFFICIENT | | | |
| ETHYLENE | 98.2% | 99.7% | 100% |
| SELECTIVITIES | | | |

TABLE III-continued

| | | | |
|---|---|---|---|
| 1) Formed ethylbenzene in relation to the converted benzene | 97.8% | 99.4% | 99.6% |
| 2) Formed ethylbenzene in relation to the converted ethylene | 93.6% | 98.7% | 99.5% |

The great influence of this parameter on the catalyst selectivity can be seen thereby; as recommended within the scope of the invention, it is preferable to work with a molar ratio benzene/ethylene ranging from 7 to 12. In fact, with molar ratios benzene/ethylene lower than 7, the selectivity is relatively low. With molar ratios benzene/ethylene higher than 12, when the selectivity is good, it is necessary to adopt very high benzene recycling rates, which strongly burdens the overall economy of the process.

EXAMPLE 8

The catalyst B which has been prepared in example 3 is tested in alkylation of benzene by propene under the following operating conditions (in a reactor known as "alkylation reactor"):

| | |
|---|---|
| temperature | 220° C. |
| pressure | 3 MPa |
| hourly flow by weight of benzene is equal to 2 × catalyst weight | |
| molar ratio benzene/propene | 5 |

The charge shows the following composition by weight:

| | |
|---|---|
| propene | 9.72% |
| benzene | 90.28% |

At the reactor outlet, the obtained product has the following composition by weight:

| | |
|---|---|
| propene | — |
| benzene | 72.58% |
| cumene | 26.74% |
| di-isopropylbenzenes | 0.60% |
| tri-isopropylbenzenes | 0.06% |
| heavy aromatic HC | 0.02% |
| | 100% |

The conversion coefficients are thus the following:

| | |
|---|---|
| benzene | 19.6% |
| propene | 100% |

The selectivities are respectively the following:

| | |
|---|---|
| cumene in relation to the converted benzene | 98.2% |
| cumene in relation to the converted propene | 96.3% |

After the reaction, the product obtained in the presence of catalyst B is fractionated by distillation, and two fractions are recovered:

a 160° C.-initial point fraction containing the non converted benzene and the cumene, a fraction with a boiling point higher than 160° C. containing the polyisopropylbenzenes and the heavy aromatic hydrocarbons.

This fraction with a boiling point higher than 160° C. is thereafter subjected to a transalkylation treatment in the presence of catalyst D (prepared in example 4) under the following operating conditions (in a reactor known as "transalkylation reactor"):

| | |
|---|---|
| temperature | 330° C. |
| pressure | 3 MPa |
| flow rate by weight of charge (polyisopropylbenzenes + heavy hydrocarbons + additional benzene stemming from the product of the alkylation reaction) is equal to 1 × catalyst weight | |
| molar ratio benzene/polyisopropylbenzenes | 10. |

The charge (for the transalkylation treatment) has thus the following composition by weight:

| | |
|---|---|
| benzene | 3.19 |
| di-isopropylbenzenes | 0.60 |
| tri-isopropylbenzenes | 0.06 |
| heavy aromatic HC | 0.02 |
| | 3.87. |

At the transalkylation reactor outlet, the obtained product shows the following composition by weight:

| | |
|---|---|
| benzene | 2.91 |
| cumene | 0.83 |
| di-isopropylbenzenes | 0.07 |
| tri-isopropylbenzenes | 0.02 |
| heavy aromatic HC | 0.04 |
| | 3.87. |

The overall results combining the two stages of alkylation on one hand and of transalkylation on the other hand are the following:

| | |
|---|---|
| benzene conversion coefficient | 19.9% |
| propene conversion coefficient | 100% |
| cumene selectivity in relation to the converted propene | 99.3% |
| cumene selectivity in relation to the converted benzene | 99.7%. |

We claim:

1. A process for producing at least one alkylbenzene comprising in a first stage reacting benzene with a charge comprising at least one aliphatic mono-olefin in the presence of at least one catalyst based on a dealuminized Y zeolite having a molar ratio $SiO_2/Al_2O_3$ ranging from 8 to 70; fractionating resultant product to separately recover a first fraction containing non-converted benzene and at least one mono-alkylbenzene, and a second fraction containing at least one polyalkylbenzene; in a second stage reacting at least part of said second fraction with benzene in contact with at least one catalyst based on a dealuminized mordenite with a total atomic ratio Si/Al ranging from 20 to 80; and recovering at least one mono-alkylbenzene.

2. A process according to claim 1 wherein at least part of the benzene reacted with at least part of said second fraction consists of said non converted benzene stemming from said first fraction.

3. A process according to claim 1 wherein said dealuminized Y zeolite has a molar ratio of $SiO_2/Al_2O_3$ ranging from about 12 to 40.

4. A process according to claim 1 wherein each catalyst contains a matrix.

5. A process according to claim 1 wherein each catalyst is arranged in a fixed bed.

6. A process according to claim 1 wherein unreacted polyalkylbenzenes from the second stage are recycled in this stage.

7. A process according to claim 1 wherein said charge comprises 0.1 to 2.0% by weight of carbon oxide.

8. A process according to claim 1 wherein said charge is a catalytic cracking effluent.

9. A process for producing ethylbenzene according to claim 1 wherein, during the reaction of benzene with a charge containing ethylene, the molar ratio of benzene/ethylene ranges from 7 to 12.

10. A process for producing cumene according to claim 1 wherein, during the reaction of benzene with a charge containing propene, the molar ratio of benzene/propene ranges from 3 to 7.

11. A process according to claim 1 wherein the Y zeolite is an HY acid zeolite having a sodium content lower than 0.25% by weight determined by calcination of the zeolite at 1100° C.; a crystalline parameter a of the unit cell ranging form $24.55 \times 10^{-10}$ to $24.24 \times 10^{-10}$ m; a sodium ion recovery capacity $C_{Na}$ per 100 g of modified, neutralized, calcined zeolite, higher than about 0.85; a specific surface higher than 400 m$^2$/g; a steam adsorption capacity at 25° C. at a partial pressure of 2.6 torrs, higher than about 6%; a pore sized distribution such that between 1 and 20% of the pore volume contained in the pores has a diameter ranging from $20 \times 10^{-10}$ to $80 \times 10^{-10}$ m, with the remainder of the pore volume being pores having a diameter smaller than $20^{31}$ $^{10}$ m.

12. A process according to claim 11 wherein the crystalline parameter a of the unit cell is $24.39 \times 10^{-10}$ to $24.26 \times 10^{-10}$ m; the specific surface is higher than about 550 m$^2$/g; and between 3 and 15% of the pore volume contained in the pores has a diameter from $20 \times 10^{-10}$ to $80 \times 10^{-10}$ m.

13. A process for producing ethylbenzene according to claim 2 wherein, during the reaction of benzene with a charge containing ethylene, the molar ratio of benzene/ethylene ranges from 7 to 12.

14. A process for producing ethylbenzene according to claim 3 wherein, during the reaction of benzene with a charge containing ethylene, the molar ratio of benzene/ethylene ranges from 7 to 12.

15. A process for producing ethylbenzene according to claim 6 wherein, during the reaction of benzene with a charge containing ethylene, the molar ratio of benzene/ethylene ranges from 7 to 12.

16. A process for producing ethylbenzene according to claim 11 wherein, during the reaction of benzene with a charge containing ethylene, the molar ratio of benzene/ethylene ranges from 7 to 12.

17. A process for producing ethylbenzene according to claim 12 wherein, during the reaction of benzene with a charge containing ethylene, the molar ratio of benzene/ethylene ranges from 7 to 12.

18. A process according to claim 1, wherein the mordenite has an Si/Al molar ratio of at least 60.

* * * * *